United States Patent
Magnus et al.

(10) Patent No.: US 6,667,410 B2
(45) Date of Patent: Dec. 23, 2003

(54) CONVERSION OF α,β-UNSATURATED KETONES AND α,β-UNSATURATED ESTERS INTO α-HYDROXY KETONES AND α-HYDROXY ESTERS USING MN(III) CATALYST, PHENYLSILANE AND DIOXYGEN

(75) Inventors: Philip D. Magnus, Austin, TX (US); Andrew H. Payne, Ware (GB)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/952,326

(22) Filed: Sep. 14, 2001

(65) Prior Publication Data

US 2002/0120170 A1 Aug. 29, 2002

Related U.S. Application Data

(60) Provisional application No. 60/233,351, filed on Sep. 18, 2000.

(51) Int. Cl.[7] .......................... C07J 5/00; C07C 49/207; C07C 49/213
(52) U.S. Cl. ....................... 552/585; 568/377; 568/388; 549/200
(58) Field of Search ........................... 552/585; 568/377, 568/388; 549/200

(56) References Cited

U.S. PATENT DOCUMENTS

| | | |
|---|---|---|
| 3,056,809 A | 10/1962 | Barton et al. |
| 3,444,160 A | 5/1969 | Walker et al. |

OTHER PUBLICATIONS

Bailey et al., "Compounds related to the steroid hormones. Part IX. Oxygenation of steroid ketones in strongly basic medium: a new method of preparation of 17α–Hydroxy–pregnan–20–ones," *Chem. Soc.*, 307:1578–1591, 1962.
Birmingham et al., "Near–infrared absorption spectra of hydroxylated steroids and other alcohols," *Steroids*, 1:463–494, 1963.
Inoki et al., "A new and facile method for the direct preparation of α–Hydroxycarboxylic acid esters from α,β–Unsaturated carboxylic acid esters with molecular oxygen and phenylsilane catalyzed by Bis(dipivaloylmethanato) manganese (II) complex," *Chem Lett.*, 1869–1872, 1990..
Jacobsen et al., "highly enantioselective epoxidation catalysts derived from 1,2–diaminocyclohexane," *J. Am. Chem. Soc.*, 113:7063–7064, 1991.
Janoski et al., "Selective 3–(o–Carboxymethyl)Oxime Formation in steroidal 3,20–diones for hapten immunospecificity," *Steroids*, 23:1:49–64, 1974.
Keinan and Perez, "Silicon hydrides and molybdenum (0) catalyst: a novel approach for conjugate reduction of α,β–unsaturated carbonyl compounds," *J. Org. Chem.*, 52:2576–2580, 1987.
Lipshutz et al., "A convenient, efficient method for conjugate reductions using catalytic quantities of Cu(I)," *Tetrahedron Lett.*, 39:4627–4630, 1998.
Magnus et al., "Synthesis of the Kopsia alkaloids (±)–11, 12–demethoxylahadinine B, (±) kopsidasine and (±)–kopsidasine–N–oxide," *Tetrahedron Lett.*, 41:2077–2081, 2000.
Mahoney et al., "Selective hydride–mediated conjugate reduction of α,β–unsaturated carbonyl compounds using [(Ph$_3$P)CuH]$_6$," *J. Am. Chem. Soc.*, 110:291–293, 1988.
Pence et al., "Synthesis structural studies, and magnetic exchange interactions in low–valent manganese alkoxide cubes," *Inorg. Chem.*, 35:3069–3072, 1996.
Semmelhack et al., "Reductions of conjugated carbonyl compouds with copper hydride—Preparative and mechanistic aspects," *J. Org. Chem.*, 42(19):3180–3188, 1977.
Taft et al., "Iron and Manganese alkoxide cubes," *J. Am. Chem. Soc.*, 115:11753–11766, 1993.
Zürcher, "Protonenresonanzspektroskopie und steroidstruktur I. Das C–19–Methylsignal in Funktion der Substituenten," *Helv. Chim. Acta.*, 44:1380–1395, 1961. Summary in English. (Abstract Only).
Zürcher, "Protonenresonanzspektroskopie und Steroidstruktur II. Die lage der C–18– und C–19–Methylsignale in abhangigkeit von den substituenten am steroidgerust," *Helv. Chim. Acta.*, 46:2054–2088, 1963. Summary in English. (Abstract Only).

*Primary Examiner*—Barbara P. Badio
(74) *Attorney, Agent, or Firm*—Fulbright & Jaworski L.L.P.

(57) ABSTRACT

The present invention provides a novel process for the conversion of α,β-unsaturated ketones. This invention is an improvement over existing processes in that it operates at neutral reaction conditions that prevent the formation of side reactions and that is a single step, which proceeds with complete selectivity and gives a yield that is approximately 30% higher than the currently used processes. An example of this process is the conversion of 16-dehydroprogesterone into 17 α-hydroxyprogesterone.

56 Claims, 1 Drawing Sheet

Mn(dpm)3 from X-ray coordinates

CONVERSION OF α,β-UNSATURATED KETONES AND α,β-UNSATURATED ESTERS INTO α-HYDROXY KETONES AND α-HYDROXY ESTERS USING MN(III) CATALYST, PHENYLSILANE AND DIOXYGEN

The application claims priority to U.S. Provisional Application Serial No. 60/233,351, filed on Sep. 18, 2000.

BACKGROUND OF THE INVENTION

1. Field of the Invention

The invention relates generally to the conversion of α,β-unsaturated ketones and α,β-unsaturated esters to α-hydroxy ketones and α-hydroxy esters.

2. Description of Related Art

Methods for the conversion of α,β-unsaturated ketones and α,β-unsaturated esters to α-hydroxy ketones and α-hydroxy esters are known in the art. Conjugate reduction of α,β-unsaturated ketones using $Na(MeOCH_2CH_2O)_2AlH_2/CuBr$ (Semmelhack et al., 1977); $((Ph_3P)CuH)_6$ (Mahoney et al., 1988); $((Ph_3P)CuH)_6/n\text{-}Bu_3SnH$ or $PhSiH_3$ (Lipshutz et al., 1998); and $PhSiH_3/Mo(CO)_6$ (Keinan et al., 1987) are typically followed by oxidation at the α-position to initially produce a mixture of α-hydroperoxyketone and α-hydroxyketone. The hydrosilylation of enones was done by Ojima et al. (1975). Fe—H based reagents were used by Noyori et al. (1972), Cainelli et al, (1973), Yamashita et al., (1975), and Collman et al. (1978). For a general review of conjugate reductions, see Comprehensive Organic Synthesis, Vol 8. p. 523. Ed Trost, B. M.; Fleming, I. Pergamon Press, 1991.

In 1990 Inoki et al. reported a single step method for converting an α,β-unsaturated ester into an α-hydroxy ester. A number of simple α,β-unsaturated esters were treated with a catalytic amount of what was believed to be bis(dipivaloylmethanato) manganese(II) (abbreviated to $Mn(dpm)_2$)/$PhSiH_3$/$O_2$) in isopropanol at 0° C., and obtained (after work-up with aqueous $Na_2S_2O_3$) the saturated α-hydroxyester in good yield.

One economically important conversion is the conversion of 16-dehydroprogesterone 3 into 17 α-hydroxyprogesterone 4. This transformation of an α,β-unsaturated ketone to an α-hydroxy ketone has been the subject of a number of patents (U.S. Pat Nos. 3,056,809, 3,444,160) and papers (Bailey et al., 1962). However, in each of these cases, a multi-step route was undertaken for the conversion.

17 α-hydroxyprogesterone is a synthetic replacement for progesterone and is commonly used as a contraceptive and has a number of other uses in hormonal treatments. Therefore, there is a need for a method that is able to produce 17 α-hydroxyprogesterone and other α-hydroxyketones and esters using a single step.

A route for the conversion to α,β-unsaturated ketones or α,β-unsaturated esters to α-hydroxy ketones or α-hydroxy esters which requires only a single step under mild reaction conditions would be advantageous over the art. Known reaction routes for this conversion use basic conditions which cause the formation of 17-keto derivatives and ring D-homo rearrangements. They also involve a number of different steps which will often cause a decrease in yield or an increase in cost. It would therefore be desirable to have a method for converting α,β-unsaturated ketones or α,β-unsaturated esters into an α-hydroxy ketones or α-hydroxy esters that does not have these limitations.

SUMMARY OF THE INVENTION

This invention involves a method for converting α,β-unsaturated ketones and α,β-unsaturated esters into an α-hydroxy ketones or α-hydroxy esters. β,β-disubstituted ketones or esters can also be converted by the method of this invention. The reaction operates at neutral reaction conditions that prevent the formation of side reactions in a single step, which proceeds with excellent selectivity and gives a yield that is approximately 30% higher than the currently used processes. The conversion comprises: obtaining said α,β-unsaturated ketone or ester; obtaining a catalyst; obtaining a reducing agent; combining said ketone or ester, said catalyst and said reducing agent in the presence of dioxygen and a solvent or solvent mixture to form an α-hydroperoxyketone or α-hydroperoxyester; and reducing said α-hydroperoxyketone or ester to an α-hydroxyketone or ester with a reductive work-up.

The catalyst of this invention is of the structure:

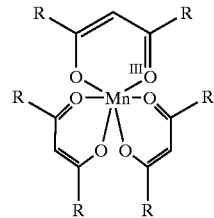

where each R is independently hydrogen, a $C_1$–$C_{20}$ linear branched or cyclic alkyl, hydroxyalkyl, glycol, polyglycol, amino, nitro, halo, cyano, aryl, heteroaryl, thio, thioalkyl, amide, ester, acyl, or carboxy. In a preferred embodiment of the invention, each R of the catalyst is the same and R is $C_1$–$C_4$ linear or branched alkyl. Preferably, at least one R is —H, —$CH_3$, —$CH_2CH_3$, —$CH_2CH_2CH_3$, —$CH_2(CH_3)_2$, —$CH_2CH_2CH_2CH_3$, —$CH_2(CH_3)CH_2CH_3$, —$CH_2CH_2(CH_3)_2$, $CH_2(CH_3)_3$, —$NO_2$, —$NH_2$, —$OCH_3$, —$O(CH_2)_n CH_3$, wherein n=0–20, and —$CO(CH_2)_n$ wherein n=0–20. In a preferred embodiment of the invention, at least one R is —$O(CH_2)_n CH_3$ and $0 \leq n \leq 20$, or more preferably —$OCH_3$. In yet another embodiment, at least one R is $NR'_2$ and R' is hydrogen or $C_1$–$C_{20}$ linear, branched or cyclic alkyl, or more preferably —$NH_2$. In the most preferred embodiment of the invention, the catalyst is tris(dipivaloylmethanato) manganese(III).

The reducing agent can be a silane, or more preferred diphenyl silane or polymethylhydrosiloxane. The most preferred reducing agent is phenyl silane.

The reductive work-up can include any reaction that causes the reduction of an α-hydroperoxyketone or ester to an α-hydroxyketone or ester. The preferred reducing agent is $P(OEt)_3$ or $P(OMe)_3$.

Solvents contemplated for this invention include alcohols such as isopropanol, tert-butyl alcohol or a mixture of an alcohol and another solvent such as 1,2-dichloroethane, dichloromethane or methylene chloride.

The substrate can be any α,β-unsaturated ketone or α,β-unsaturated ester. The carbon of the α,β-unsaturated ketone or ester can be part of a ring system. A preferred α,β-unsaturated ketone is 16-dehydroprogesterone.

Reaction conditions such as temperature, pressure, and time of the reaction may vary. The preferred temperature is between 0° C. and 25° C.

Contemplated in this invention is the conversion of 16-dehydroprogesterone to 17 α-hydroxy progesterone comprising: obtaining said α,β-unsaturated ketone or ester; obtaining a catalyst of the structure:

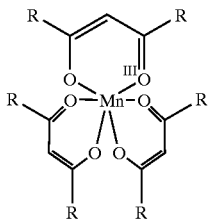

where R is described above; obtaining a reducing agent; combining said ketone or ester, said catalyst and said reducing agent in the presence of dioxygen and a solvent or solvent mixture to form an α-hydroperoxyketone; and reducing said α-hydroperoxyketone to an α-hydroxyketone.

Another aspect of this invention is the reduction of β,β-disubstituted ketone or ester comprising: i) obtaining said β,β-disubstituted ketone or ester; ii) obtaining the catalyst tris(dipivaloylmethanato)manganes(III); iii) obtaining a reducing agent; iv) combining said ketone or ester, said catalyst and said reducing agent in the presence of dioxygen and a solvent or solvent mixture to produce a hydridic reagent capable of reducing said β,β-disubstitued ketone or ester. Preferred β,β-disubstituted ketone or ester include β-ionone and 16-methyl dehydroprogesterone.

BRIEF DESCRIPTION OF THE DRAWINGS

The following drawing forms part of the present specification and is included to further demonstrate certain aspects of the present invention. The invention may be better understood by reference to this drawing in combination with the detailed description of specific embodiments presented herein.

DESCRIPTION OF ILLUSTRATIVE EMBODIMENTS

Figure 1:
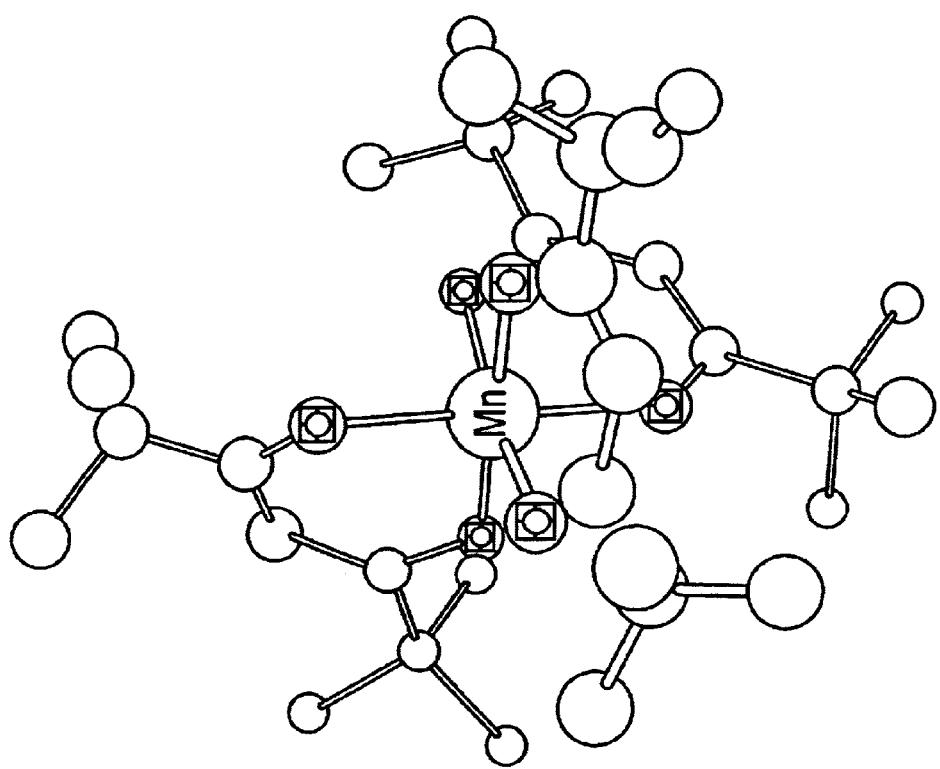
FIG. 1 X-ray structure of tris(dipivaloylmethanato) manganese(III)(Mn(dpm)$_3$)

The present invention generally relates to the treatment of α,β-unsaturated ketones or α,β-unsaturated esters with a catalyst system including tris(dipivaloylmethanato) manganese(III)/PhSiH$_3$/O$_2$ to form α-hydroxy ketones or α-hydroxy esters. The inventors report applications of this reaction to a number of α,β-unsaturated ketones. Furthermore, the inventors have found that the hydridic character of the putative reagent HMn(dpm)$_2$ is substantially increased in the presence of dioxygen and produces a new hydridic reagent that is capable of reducing β,β-disubstituted enones.

A. Progesterone and Progestins

A useful reaction of the present invention involves the conversion of 16-dehydroprogesterone to 17 α-hydroxy progesterone. This reaction product can be used as a synthetic replacement for progesterone. Progesterone is a 21 carbon steroid produced primarily by the corpus luteum and the extraembryonic membranes and is produced by conversion of cholesterol to pregnenolone which is then converted on to progesterone. This conversion occurs as a result of the side chain (cytochrome P450) cleavage enzymes.

Progestins are a type of steroidal sex hormone the most important of which is progesterone. Synthetic forms of progesterone designed to have similar physiological functions as progesterone are also known as progestins. Natural progesterone has no oral efficacy because gastric fluid destroys most of the steroid and the small amount that is absorbed is destroyed by the liver. Synthetic progestins which overcome this problem include: hydroxyprogesterone, norethindrone (19-nortestosterone), norethynodrel, ethynodiol, norgestrel, methoxyprogesterone acetate (C-21 progestin) and megestrol acetate.

Most progestins are used as contraceptives, but a number of other therapeutic uses have been found including: (1) regulate the menstrual cycle and treat unusual stopping of the menstrual periods (amenorrhea); (2) help pregnancy occur during egg donor or infertility procedures in women who do not produce enough progesterone; (3) help maintain a pregnancy when not enough of it is made by the body; (4) treat endometriosis or unusual and heavy bleeding of the uterus (dysfunctional uterine bleeding) by starting or stopping the menstrual cycle; (5) help treat cancer of the breast, kidney, or uterus by helping to change the cancer cell's ability to react to other hormones and proteins that cause tumor growth; (6) test the body's production of certain hormones such as estrogen; and (7) treat loss of appetite and severe weight or muscle loss in patients with acquired immunodeficiency syndrome (AIDS) or cancer by causing certain proteins to be produced that cause increased appetite and weight gain.

B. Tris(dipivaloylmethanato)manganese(III)(Mn(dpm)$_3$)

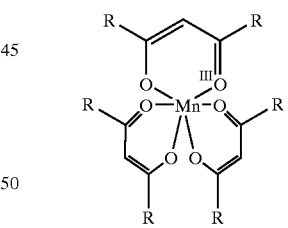

The synthesis of acetylacetonatomanganese(II) complexes in air is known to be somewhat ligand dependent and can give rise to the tris(acetylacetonato)manganese(III) adducts (Fernelius) et al., 1957; Fackler et al., 1966, Fevason et al., 1972). Consequently, when what is described as the Mn(dpm)$_2$ complex (Hammond et al., 1959) was prepared, an olive green-brown solid more reminiscent of a Mn(III) complex (Charles, 1963) was obtained. X-ray quality crystals of the complex were grown in isopropanol and revealed that the structure is an octahedral complex Mn(dpm)$_3$, as shown in FIG. 1. This structure is similar to Mn(acac)$_3$ (Morosin et al., 1964).

Scheme 1

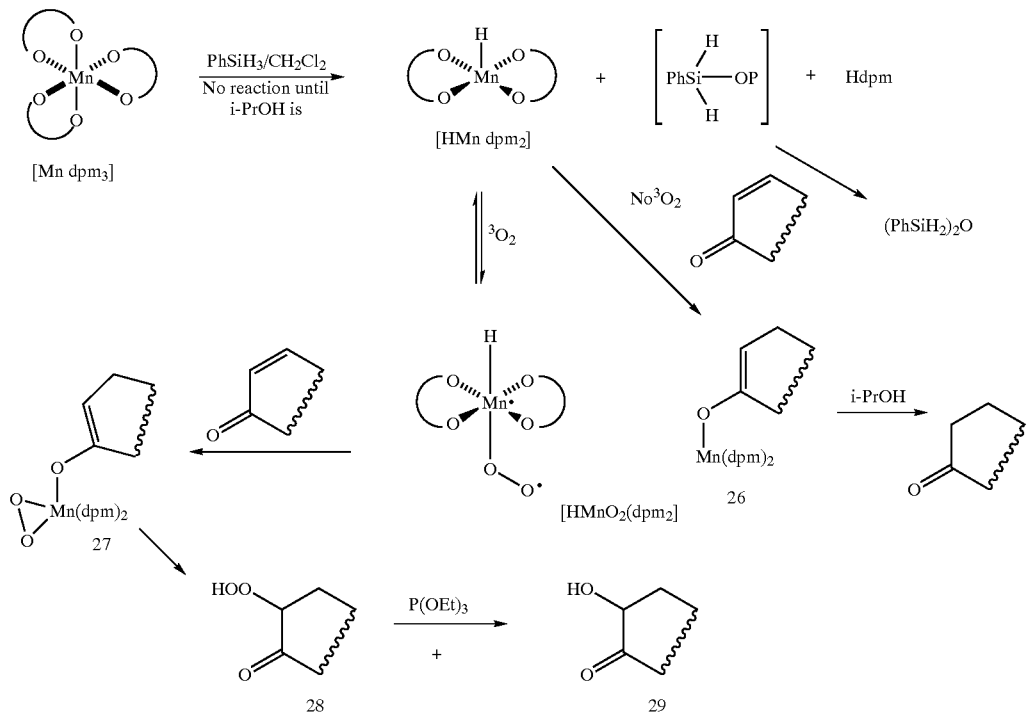

C. Substrates and Reactants for Conversion Reaction

The conversion of this invention will reduce α,β-unsaturated ketones or esters of the general formula:

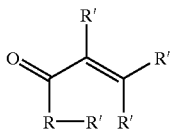

where R is C or O and each R' is independently hydrogen, a $C_1$–$C_{50}$ linear branched or cyclic alkyl, hydroxyalkyl, heteroaryl, thio, thioalkyl, amide, ester, acyl, carboxy, glycol, polyglycol, amino, nitro, halo, cyano, aryl, thio, or thioalkyl. Two or more R' may form a ring system which may include a single or multiple rings. A non-limiting list of examples of α,β-unsaturated ketones is included in Table I.

Attempts to discover the fate of phenylsilane, the hydride source, indicated that formation of phenylisopropyl(oxy) silane was inconclusive. Under the reaction conditions (and work-up) phenylisopropyl(oxy)silane would have been converted into diphenyldisiloxane (Mitzel et al., 1992; Harvey et al., 1957), which was detected ($^1$H NMR, authentic sample), but in relatively small amounts.

A variety of proton sources that are known in the art can be in this reduction, non-limiting examples include isopropanol, ethanol, 1-propanol, 1-butanol, isobutanol, tert-butanol, and pentanol. It was found that secondary alcohols are the most productive. Isopropanol is the preferred proton source. When methanol was substituted for isopropanol there was rapid gas evolution ($H_2$), no reduction of 7, and the formation of $PhSi(OMe)_3$ from the phenyl silane. When tert-butyl alcohol was used as the proton source, the reduction of α,β-unsaturated ketones or α,β-unsaturated esters proceeded, but was very slow. Therefore, isopropanol is the preferred alcohol to use as a proton source. The solvent can consist of the proton source or the proton source mixed with another solvent such as dichloromethane, 1,2-dichloroethane, 1,1-dichloroethane, methylene chloride, methanol, ethanol, or propanol. A mixture of isopropanol and 1,2-dichloroethane is a preferred solvent system.

The inventors have also observed that the way in which the reaction flask is washed influences the product distribution. This indicates that the presence of water or other contaminants on the surface of the reaction container alters the reaction process. For example, treatment of 13 in a flask washed with acetone (dried) under the standard conditions gave 14 (20%) and substantial amounts of 2-nonanone (60%). Whereas, treatment of 13, as before, but in a flask washed with Alconox® (pH 9) followed by acetone, gave 14 (70%) and only traces of 2-nonanone (<5%). It appears that the protic surface of the flask is capable of converting 26 (Scheme 1) into the saturated derivative competitively with α-hydroperoxide 28 formation.

It was found that the presence of dioxygen in the reaction is important for the conjugate reduction of the instant invention to occur. Treatment of the α,β-unsaturated ketones with $Mn(dpm)_3$ without dioxygen present, as further described in example 4, resulted in saturation of the ketone.

Any reducing agent that is capable of reducing the catalyst of this invention can be used. The use of a number of reducing agents was examined, and it was found that, although other silanes would reduce the catalyst, the preferred reducing agent is phenyl silane. Diphenyl silane was found to reduce the α,β-unsaturated ketones or α,β-unsaturated esters, however, the reaction was very slow. The reaction did not work with triethyl silane, and polymethylhydrosiloxane was also very slow and incomplete.

After the conversion of α,β-unsaturated ketones and esters to α-hydroperoxyketones or α-hydroperoxyesters, the substrate must be reduced to α-hydroxyketones and esters.

There are many known methods of reducing these intermediates which can be used in this invention. Non-limiting examples of agents contemplated for reductive work-up include $P(OEt)_3$, $Na_2S_2O_3$, $H_2/Pd/C$; $Me_2S$, $Ph_3P$, and Xn/AcOH.

D. Determination of Reaction Mechanism

Deuterium labeling studies in the absence of oxygen indicated that the conjugate hydride addition step is irreversible. Furthermore, β,β-disubstituted enones are not reduced to their saturated derivatives in the absence of oxygen. For example, exposure of mesityl oxide 21 with $Mn(dpm)_3/PhSiH_3$/i-PrOH in the absence of oxygen did not produce any reaction, whereas the same conditions in the presence of oxygen gave 22. Likewise 23 was inert to reduction until oxygen was introduced, and this resulted in the formation of 24 and 24a (64%, 4:1), (Scheme 2). Treatment of β-ionone 9 with $Mn(dpm)_3$/$PhSiH_3$/i-PrOH gave 25 (25%, large amounts of 9), whereas, the same reaction in the presence of oxygen gave 10.

reflect the relative amounts of O—Mn versus O—O cleavage in 27 (Scheme 1). Vedejs et al. (1974) demonstrates this reaction with a molybdenum peroxy analog. Over a period of about 5 h at room temperature the peroxy-hydride $HMnO_2(dpm)_2$ loses both reducing and oxidizing capability.

It should be noted that Lippard has characterized the "bright yellow" adduct $[Mn_4(OEt)_4(EtOH)_2(dpm)_4]$ and other similar Mn(II) adducts as alkoxide cubes with a $Mn_4O_4$ cubic core (Taft et al., 1993; Pence et al., 1996). The inventors have prepared $[Mn_4(OEt)_4(EtOH)_2(dpm)_4]$ according to the Lippard procedure, and when a yellow ethanol solution of this catalytic complex is treated with $PhSiH_3$ (1.3 eq)/$O_2$/4-oxoisophorone, the solution becomes olive green-brown and 4-oxoisophorone 7 (entry 4) is converted into 8 (56%). The salenMn(III)Cl type of catalyst did not produce any reaction (Jacobsen et al., 1991).

E. Definitions

With reference to the substituents contemplated for use in accordance with the present invention, alkyl may be of the Scheme 2

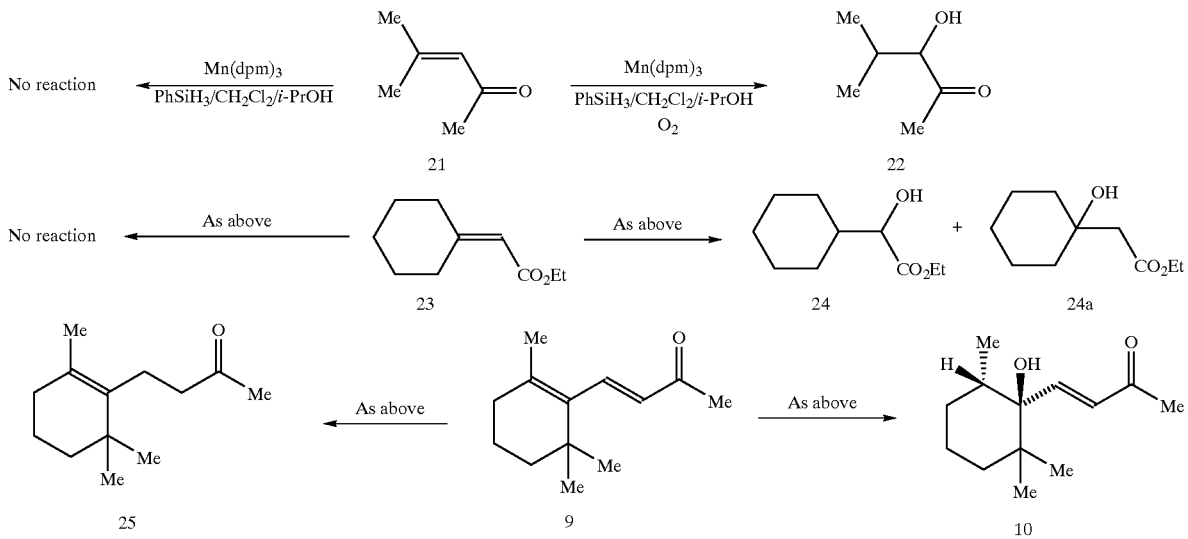

Treatment of a dark olive-green solution of $Mn(dpm)_3$ in dichloromethane with stoichiometric amounts of $PhSiH_3$ (2152 cm$^{-1}$) produced no change (IR), but addition of ispropanol to the solution rapidly 1-min) produced a pale yellow solution that exhibited an IR absorption at 2168 cm$^{-1}$. This is consistent with the formation of $HMn(dpm)_2$.

To explain these observations, especially the acceleration of conjugate reduction when oxygen is present, appears to require two distinct reducing agents. The $HMn(dpm)_2$ reagent reacts with enones to produce 26 which is protonated to give the saturated ketone, (Scheme 1). This reagent does not reduce β,β-disubstituted enones. If $HMn(dpm)_2$ (pale yellow-green) is exposed to oxygen it immediately turns dark green-brown (under vacuum the pale yellow green color returns), and this reagent does reduce β,β-disubstituted enones (Scheme 2 and entry 5, Table 1). The inventors suggest that the new manganese adduct formed in the presence of oxygen is $HMnO_2(dpm)_2$ (Kitajuma et al., 1994; VanAtta et al., 1987) which reduces enones to the manganeseperoxyenolate 27, and subsequently produces 28 and 29. In all of the reactions in the presence of oxygen the α-hydroperoxy ketone 28 is produced along with the α-hydroxy ketone 29 in varying proportions which may repeating unit —$(CH_2)_nCH_3$. The number of repeating units within an alkyl substituent may be up to fifty, preferably up to 20 and more preferably from 0–10. Representative examples of alkanes include methane, ethane, straight chain branched or cyclic isomers of propane, butane pentane hexane, octane, nonane and decane. Representative examples of substituted alkyls include alkyls substituted by two or more functional groups as described herein. Hydroxyalkyls includes alcohols of alkyl groups as defined previously. Representative examples of hydroxyalkyls include alcohols of methane, ethane, straight chain branched or cyclic isomers of propane, butane, pentane hexane, octane, nonane and decane. Hydroxyalkyl is meant to include glycols and polyglycols. Representative examples of glycols include diols of ethane, straight-chain, branched or cyclic isomers of propane, butane, pentane hexane, octane, nonane and decane. Representative examples of polyglycols include polyethylene glycol, polypropylene diol and polybutylene diol. Representative examples of oxyalkyls include the alkyl groups defined herein above having ether linkages.

As used herein, aryl refers to a compound whose molecules having either the 6-carbon ring of benzene or the condensed 6-carbon rings of the other aromatic derivatives.

Representative examples include benzene, naphthalene, phenanthrene, and anthracene. A heteroaryl compound, as used herein, refers to a compound which contains more than one kind of atom in an aromatic ring. Representative examples include pyridine, pyrimidine, furan, thiophene, pyrrole and imidazole.

Representative examples of amines include primary, secondary and tertiary amines of an alkyl as described hereinabove.

Representative examples of carboxy groups include carboxylic acids of the alkyls described above as well as aryl carboxylic acids such as benzoic acid. Representative examples of carboxyamides include primary carboxyamides (RCONH$_2$), secondary (RCONHR') and tertiary (RCONR'R") carboxyamides where each of R' and R" is a functional group as described herein and the carboxy group is as defined herein above.

Representative examples of ester groups include compounds of the form RCOR' where the R group is an alkyl as described herein above and where R' is a functional group as described herein. Representative examples of acyl groups include acyl derivatives RCO— or ArCO—, wherein R is an alkyl as described herein above and Ar is an aryl group as defined herein.

As used herein the specification, "a" or "an" may mean one or more. As used herein in the claim(s), when used in conjunction with the word "comprising", the words "a" or "an" may mean one or more than one. As used herein "another" may mean at least a second or more.

F. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Synthesis of Tris(dipivaloylmethanato)manganese (III) Complex (Mn(dpm)$_3$

To a vigorously stirring mixture of manganese (II) sulfate monohydrate (1.5 g, 9 mmol, 1.0 eq) and 2,2,6,6-tetramethyl-3,5-heptanedione (5.0 g, 27 mmol, 4.0 eq) in a mixture of water (30 mL) and methanol (6 mL) at room temperature was added concentrated ammonia solution (12 mL) dropwise, resulting in the immediate formation of a dark olive green/brown precipitate. The precipitate was filtered off, washed with water (3×10 mL) and dried in vacuo for 24 h to give Mn(dpm)$_3$ (4.9 g, 90%). X-ray quality crystals of the complex were obtained from isopropanol and revealed that the structure is an octahedral complex of tris(dipivaloylmethanato)manganes(III) (abbreviated as Mn(dpm)$_3$, similar to Mn(acac)$_3$ (Morosin et al., 1964).

EXAMPLE 2

Reduction of Ketones with Mn(dpm)$_3$(cat)/PhSiH$_3$/O$_2$/i-PrOH

The conjugate reduction of α,β-unsaturated ketones followed by oxidation of in situ generated enolates gives α-hydroxyketones using Mn(dpm)$_3$(cat)/PhSiH$_3$/O$_2$/i-PrOH. Treatment of the α,β-unsaturated ketones listed in Table 1 with Mn(dpm)$_3$ (3 mol %)/PhSiH$_3$/isopropanol at 0° to 25° C. under an oxygen balloon resulted in conjugate reduction.

TABLE 1

| Entry | Substrate | Conditions | Product | Yield |
|---|---|---|---|---|
| 1 | *structure 1* | Mn(dpm)$_3$(3 mol %), PhSiH$_3$(2 eq), i-PrOH (0.2M conc. of 1), O$_2$. | *structure 2* | 78% |
| 2 | *structure 3* | 1. Mn(dpm)$_3$(3 mol %), PhSiH$_3$(1.3 eq), i-PrOH/DCE, O$_2$. 2. P(OEt)$_3$(1.1 eq), ClCH$_2$CH$_2$Cl | *structure 4* | 85% |
| 3 | *structure 5* | 1. Mn(dpm)$_3$(3 mol %), PhSiH$_3$(1.3 eq), i-PrOH/DCE, O$_2$. 2. P(OEt)$_3$(1.1 eq), ClCH$_2$CH$_2$Cl | *structure 6* | 59% |

TABLE 1-continued

| Entry | Substrate | Conditions | Product | Yield |
|---|---|---|---|---|
| 4 | 7 | 1. Mn(dpm)$_3$(3 mol %), PhSiH$_3$(1.3 eq), i-PrOH/DCE, O$_2$. 2. P(OEt)$_3$(1.1 eq), ClCH$_2$CH$_2$Cl | 8 | 87% |
| 5 | 9 | 1. Mn(dpm)$_3$(3 mol %), PhSiH$_3$(1.3 eq), i-PrOH/DCE, O$_2$. 2. P(OEt)$_3$(1.1 eq), ClCH$_2$CH$_2$Cl | 10 | 51% |
| 6 | 11 | 1. Mn(dpm)$_3$(3 mol %), PhSiH$_3$(1.3 eq), i-PrOH/DCE, O$_2$. 2. P(OEt)$_3$(1.1 eq), ClCH$_2$CH$_2$Cl | 12 | 50% |
| 7 | 13 | 1. Mn(dpm)$_3$(3 mol %), PhSiH$_3$(1,3 eq), i-PrOH/DCE, O$_2$. 2. P(OEt)$_3$(1.1 eq), ClCH$_2$CH$_2$Cl | 14 | 73% |
| 8 | 15 | 1. Mn(dpm)$_3$(3 mol %), PhSiH$_3$(1.3 eq), i-PrOH/CH$_2$Cl$_2$(1:4), O$_2$, 2. P(OEt)$_3$(1.1 eq). | 16 | >95% |
| 9 | 17 | 1. Mn(dpm)$_3$(3 mol %), PhSiH$_3$(1.3 eq), i-PrOH/CH$_2$Cl$_2$(1:4), O$_2$. 2. P(OEt)$_3$(1.1 eq). | 18 | >95% |
| 10 | 19 | 1. Mn(dpm)$_3$(3 mol %), PhSiH$_3$(1.3 eq), i-PrOH/CH$_2$Cl$_2$(1:4), O$_2$. 2. P(OEt)$_3$(1.1 eq). | 20 | 70% |

Further information on the compounds produced in these reactions can be found in the following references: 2 Kido et al., 1995; 4 (Birmingham et al., 1963; Janoski et al., 1974; Zürcher et al., 1961; Zürcher et al., 1963); 6 (Ragoussis et al., 1985; Subbaraju et al., 1992); 8 Yamazaki et al., 1988; 12 Tamura et al., 1970; 12 Hünig et al., 1979; 14 Reutrakul et al., 1980; 20 d'Angelo et al., 1975.

The examples listed in the table illustrate that the reaction proceeds in average (50%, entry 6) to excellent (>95%, entries 8 and 9) yields. The single step method described above is superior to current methods of converting α,β-unsaturated ketones or α,β-unsaturated esters into α-hydroxy ketones or α-hydroxy esters since the non-basic conditions avoid the formation of 17-keto derivatives (Siddell et al., 1966), and the ring D-homo rearrangement (Yarnell et al., 1937; Stavely et al., 1941; Shoppee et al., 1966).

Treatment of β-ionone 9 under the standard reaction conditions surprisingly gave 10 (structure by X-ray). The bulk of the remaining mass balance was 9, and efforts to drive the reaction to completion resulted in the formation of uncharacterized by-products. None of the 1,4-reduction product was observed.

EXAMPLE 3

Reduction of 16-dehydroprogesterone with Mn(dpm)$_3$(cat)/PhSiH$_3$/O$_2$/i-PrOH A particularly useful transformation is the direct one step conversion of 16-dehydroprogesterone 3 into 17α-hydroxyprogesterone 4 (85%, entry 2). Treatment of 16-dehydroprogesterone 3 with Mn(dpm)$_3$ (3 mol %), PhSiH$_3$ (1.3 eq), i-PrOH/CH$_2$Cl$_2$, O$_2$ followed by reductive work-up with P(OEt)$_3$ gave 17 α-hydroxyprogesterone 4 (85%).

To a stirred solution of 16-dehydroprogesterone 3 (0.041 g, 0.131 mmol, 1.0 equ) and Mn(dpm)$_3$ (0.002 g, 0.003 mmol, 0.02 eq) in a mixture of isopropanol (1.5 mL) and enough 1,2-dichloroethane (0.6 mL) to completely dissolve the starting material at 0° C. for 20 min. then at room temperature for 2 h under O$_2$. The solvents were removed by distillation under reduced pressure, affording a cream solid.

Purification by flash column chromatography over silica, eluting with 30% EtOAc-hexanes afforded the 17 α-hydroxyprogesterone 4 as a white crystalline solid (0.037 g, 85%) which was identical in all respects with an authentic sample.

EXAMPLE 4

Reduction of Ketones without Dioxygen

In this example, the reduction of α,β-unsaturated ketones using Mn(dpm)$_3$(cat)/PhSiH$_3$/i-PrOH where the reagent system does not contain O$_2$ is reported.

In a stoichiometric reaction a dark olive green solution of Mn(dpm)$_3$ in isopropanol at 23° C. was treated with PhSiH$_3$ to give a pale yellow solution which rapidly reduced 7 to give 8. When the same reaction was conducted with catalytic amounts of Mn(dpm)$_3$ (3 mol %) the reduction was much slower but proceeded in good yields. Table 2 lists a series of enones that were conjugatively reduced using this procedure.

TABLE 2

| Entry | Substrate | Conditions | Product | Yield |
|---|---|---|---|---|
| 1 | (structure 1) | Mn(dpm)$_3$(3 mol %), PhSiH$_3$(2 eq), i-PrOH (0.2M conc. of 1). | (structure 2) | 50% |
| 2 | (structure 3) | Mn(dpm)$_3$(3 mol %), PhSiH$_3$(1.3 eq), i-PrOH/DCE. | (structure 4) | 99% |
| 3 | (structure 7) | Mn(dpm)$_3$(3 mol %), PhSiH$_3$(1.3 eq), i-PrOH/DCE. | (structure 8) | 99% |
| 4 | (structure 9) | Mn(dpm)$_3$(3 mol %), PhSiH$_3$(1.3 eq), i-PrOH/DCE. | (structure 25) | 25% |
| 5 | (structure 30) | Mn(dpm)$_3$(3 mol %), PhSiH$_3$(1.3 eq), i-PrOH/DCE. | (structure 31) | 50% |

TABLE 2-continued

| Entry | Substrate | Conditions | Product | Yield |
|---|---|---|---|---|
| 6 | 13 | Mn(dpm)$_3$(3 mol %), PhSiH$_3$(1.3 eq), i-PrOH/DCE. | 32 | 74% |
| 7 | 15 | Mn(dpm)$_3$(3 mol %), PhSiH$_3$(1.3 eq), i-PrOH/CH$_2$Cl$_2$(1:4). | 33 | 100% |
| 8 | 17 | Mn(dpm)$_3$(3 mol %), PhSiH$_3$(1.3 eq), i-PrOH/CH$_2$Cl$_2$(1:4). | 34 | 100% |

EXAMPLE 5

Deuterium Labeling Experiments

Deuterium labeling experiments using PhSiD$_3$ converted 13 (Scheme 3) into 32d with the incorporation of one deuterium atom in the β-position. This demonstrates that the hydride addition is irreversible since if a putative Mn$^{III}$ enolate 32a could β-eliminate HMn(dpm)$_2$ (isotope effect) one would expect to accumulate 32b which would be converted into the β,β-dideuterium derivative 32c. Similarly, treatment of 7 with Mn(dpm)$_3$/PhSiD$_3$ gave 8 with incorporation of one deuterium atom. Attempts to increase the rate of reduction of 7 by conducting the reaction at slightly higher temperatures than 23° C. did not work and also lead to small amounts of 1,2-reduction to give 4-hydroxyisophorone (Zarghami et al., 2000).

As expected, β,β-disubstituted α,β-unsaturated ketones (and α,β-unsaturated esters) are not conjugatively reduced using the above conditions.

References

The following references, to the extent that they provide exemplary procedural or other details supplementary to those set forth herein, are specifically incorporated herein by reference.

Bailey, E. J.; Barton, D. H. R.; Elks, J.; Templeton, J. F. *J. Chem. Soc.* 1962, 1578.

Birmingham, M. K.; Traikov, H.; Ward, P. J. *Steroids* 1963, 1, 463.

Cainelli, G.; Panunzio, M.; Umani-Ronchi, A. *Tetrahedron Lett.* 1973, 2491.

Charles, R. G. *Inorg. Syn.* 1963, 7, 183.

Collman, J. P.; Finke, R. G.; Matlock, P. L.; Wahren, R.; Komoto, R. G.; Brauman, J. I. *J. Am. Chem. Soc.* 1978, 100, 1119.

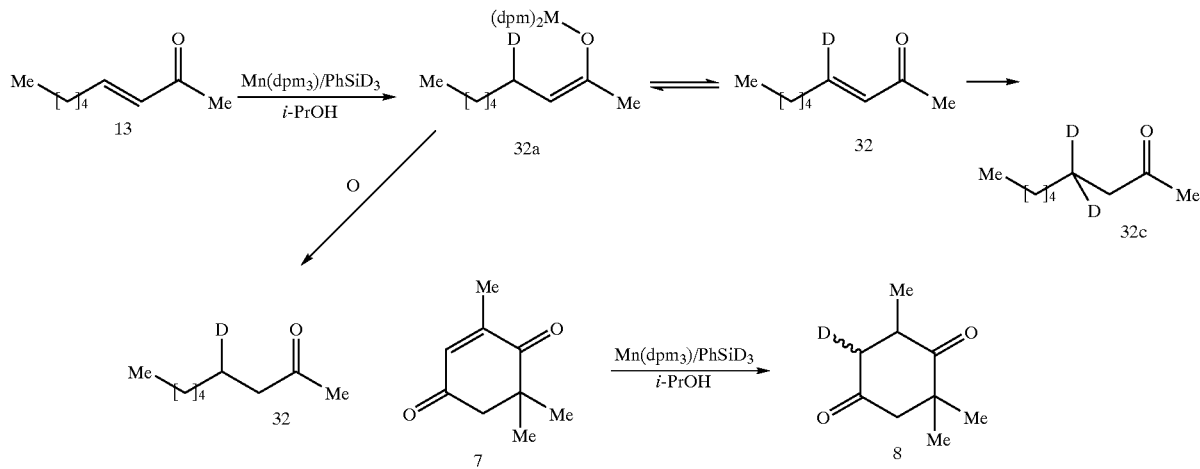

Scheme 3

Comprehensive Organic Synthesis, Vol 8. p. 523. Ed Trost, B. M.; Fleming, I. Pergamon Press, 1991.
Corriu, R. J. P.; Moreau, J. J. E. *J. Organomet. Chem.* 1976, 114, 135.
d'Angelo, *J. Bull. Soc. Chim. Fr.* 1975, 333.
Fernelius, W. C.; Bryant, B. E. *Inorg. Syn.* 1957, 5, 105.
Fackler, J. P. Jr. *Progr. Inorg. Chem.* 1966, 7, 361.
Gardner, J. N.; Carlon, F. E.; Gnoj, O. *J. Org. Chem.* 1968, 33, 3294.
Gardner, J. N.; Popper, T. L.; Carlon, F. E.; Gnoj, O.; Herzog, H. L. *J. Org. Chem.* 1968, 33, 3695.
Hammond, G. S.; Borduin, W. G.; Guter, G. A. *J. Am. Chem. Soc.* 1959, 81, 4682.
Harvey, M. C.; Nebergall, W. H.; Peake, J. S. *J. Am. Chem. Soc.* 1957, 79, 1437.
Hennig, M.; Püntener, K.; Scalone, M. *Tetrahedron: Asymmetry* 2000, 11, 1849.
Hünig, S.; Wehner, G. *Chem. Ber.* 1979, 112, 2062.
Inoki, S.; Kato, K.; Isayama, S.; Mukaiyama, T. *Chem Lett.* 1990, 1869.
Jacobsen, E. N.; Zhang, W.; Muci, A. R.; Ecker, J. R.; Deng, L. *J. Am. Chem. Soc.* 1991, 113, 7063.
Janoski, A. H.; Shulman, F. C.; Wright, G. E. *Steroids* 1974, 23, 49.
Keinan, E.; Perez, D. *J. Org. Chem.* 1987, 52, 2576.
Kido, F.; Yamaji, K.; Sinha, S. C.; Abiko, T.; Kato, M. *Tetrahedron* 1995, 51, 7697.
Kitajima, N.; Komatsuzaki, H.; Hikichi, S.; Osawa, M.; Moro-oka, Y. *J. Am. Chem. Soc.* 1994, 116, 11596.
Levason, W.; McAuliffe, C. A. *Coordination Chemistry Reviews* 1972, 7, 353.
Lipshutz, B. H.; Keith, J.; Papa, P.; Vivian, R. *Tetrahedron Lett.* 1998, 39, 4627.
Magnus, P.; Payne, A. H.; Hobson, L. *Tetrahedron Lett.* 2000, 41, 2077.
Mahoney, W. S.; Brestensky, D. M.; Stryker, J. M. *J. Am. Chem. Soc.* 1988, 110, 291.
Mitzel, N. W.; Schier, A.; Beruda, H.; Schmidbaur, H. *Chem. Ber.* 1992, 125, 1053.
Morosin, B.; Brathovde, J. R. *Acta. Cryst.* 1964, 17, 705.
Mukaiyama, T. "Oxygenation of olefins with molecular oxygen catalyzed by low valent metal complexes". The activation of dioxygen and homogeneous catalytic oxidation, Ed. Barton, D. H. R.; Martell, A. E.; Sawyer, D. T. Plenum Press, New York, 1993.
Noyori, R.; Umeda, I.; Ishigami, T. *J. Org. Chem.* 1972, 37, 1542.
Ojima, I.; Anagi, M. N.; Kogare, T.; Kumagai, M.; Horiuchi, S.; Nakatsugawa, K. *J. Organomet. Chem.* 1975, 94, 449.
Pence, L. E.; Caneschi, A.; Lippard, S. J. *Inorg. Chem.* 1996, 35, 3069.
Ragoussis, N.; Argyriadis, N.; Mamos, P. *Synthesis* 1985, 489.
Reutrakul, V.; Ratananukul, P.; Ninigirawath, S. *Chem. Lett.* 1980, 71.
Semmelhack, M. F.; Stauffer, R. D.; Yamashita, A. *J. Org. Chem.* 1977, 42, 3180.
Shoppee, C. W.; Prins, D. A. *Helv. Chim. Acta.* 1943, 26, 201.
Siddell, J.; Baddeley, G.; Edwards, J. *Chem. Ind. (London).* 1966, 25.
Stavely, H. E. *J. Am. Chem. Soc.* 1941, 63, 3127.
Subbaraju, G. V.; Manhas, M. S.; Bose, A. K. *Synthesis* 1992, 816.
Taft, K. L.; Caneschi, A.; Pence, L. E.; Delfs, C. D.; Papaefthymiou, G. C.; Lippard, S. J. *J. Am. Chem. Soc.* 1993, 115, 11753.
Tamura, S.; Nagao, M. *Agr. Biol. Chem.* 1970, 34, 1393.
U.S. Pat. No. 3,056,809, 1959. *Chem. Abstr.* 58, 4628b. Walker, B. H.
U.S. Pat. No. 3,444,160, 1967. *Chem. Abstr.* 71, 61687s.
VanAtta, R. B.; Strouse, C. E.; Hanson, L. K.; Valentine, J. S. *J. Am. Chem. Soc.* 1987, 109, 1425.
Vedejs, E. *J. Am. Chem. Soc.* 1974, 96, 5944.
Yamashita, M.; Watanabe, Y.; Mitsudo, T.; Takegami, Y. *Tetrahedron Lett.* 1975, 1867.
Yamazaki, Y.; Hayashi, Y.; Hori, N.; Mikami, Y. *Agric. Biol. Chem.* 1988, 52, 2919.
Yarnell, W. A.; Wallis, E. S. *J. Am. Chem. Soc.* 1937, 59, 951.
Zarghami, N. S.; Heinz, D. E. *Phytochemistry* 1971, 10, 2755.
Zürcher, R. F. *Helv. Chim. Acta.* 1961, 44, 1380.
Zürcher, R. F. *Helv. Chim. Acta.* 1963, 46, 2054.

What is claimed is:

1. A method for converting $\alpha,\beta$-unsaturated ketones to $\alpha$-hydroxyketones comprising:

i) obtaining said $\alpha,\beta$-unsaturated ketone;

ii) obtaining a catalyst of the structure:

where each R is independently hydrogen, a $C_1$–$C_{20}$ linear, branched or cyclic alkyl, hydroxyalkyl, glycol, polyglycol, amino, nitro, halo, cyano, aryl, heteroaryl, thio, thioalkyl, amide, ester, acyl, carboxy, —$NH_2$, —$O(CH_2)_nCH_3$ and $0 \leq n \leq 20$ or —$OCH_3$;

iii) obtaining a reducing agent;

iv) combining said ketone, said catalyst and said reducing agent in the presence of dioxygen and a solvent or solvent mixture to form an $\alpha$-hydroperoxyketone; and v) reducing said $\alpha$-hydroperoxyketone to an $\alpha$-hydroxyketone.

2. The method of claim 1, wherein at least one R is —H, —$CH_3$, —$CH_2CH_3$, —$CH_2CH_2CH_3$, —$CH(CH_3)_2$,— $CH_2CH_2CH_2CH_3$, —$CH(CH_3)CH_2CH_3$, —$CH_2CH(CH_3)_2$ or $C(CH_3)_3$.

3. The method of claim 1, wherein each R is the same and R is $C_1$–$C_4$ linear or branched alkyl.

4. The method of claim 1, wherein at least one R is —$O(CH_2)_nCH_3$ and $0 \leq n \leq 20$.

5. The method of claim 4, wherein at least one R is —$OCH_3$.

6. The method of claim 1, wherein at least one R is —$CO(CH_2)_nCH_3$ and $0 \leq n \leq 20$.

7. The method of claim 1, wherein R is $NR'_2$ and R' is hydrogen or $C_1$–$C_{20}$ linear, branched or cyclic alkyl.

8. The method of claim 7, wherein at least one R is —$NH_2$.

9. The method of claim 3, wherein the catalyst is tris (dipivaloylmethanato)manganese(III).

10. The method of claim 1, wherein the reducing agent is a silane.

11. The method of claim 10, wherein the reducing agent is phenyl silane.

12. The method of claim 10, wherein the reducing agent is diphenyl silane.

13. The method of claim 10, wherein the reducing agent is polymethylhydrosiloxane.

14. The method of claim 1, wherein P(OEt)$_3$ is used to reduce the α-hydroperoxy ketone.

15. The method of claim 1, wherein the solvent is isopropanol.

16. The method of claim 1, wherein the solvent is a mixture of isopropanol and 1,2-dichloroethane.

17. The method of claim 1, wherein the temperature is between 0° C. and 25° C.

18. The method of claim 1, wherein the α,β-unsaturated ketone is:

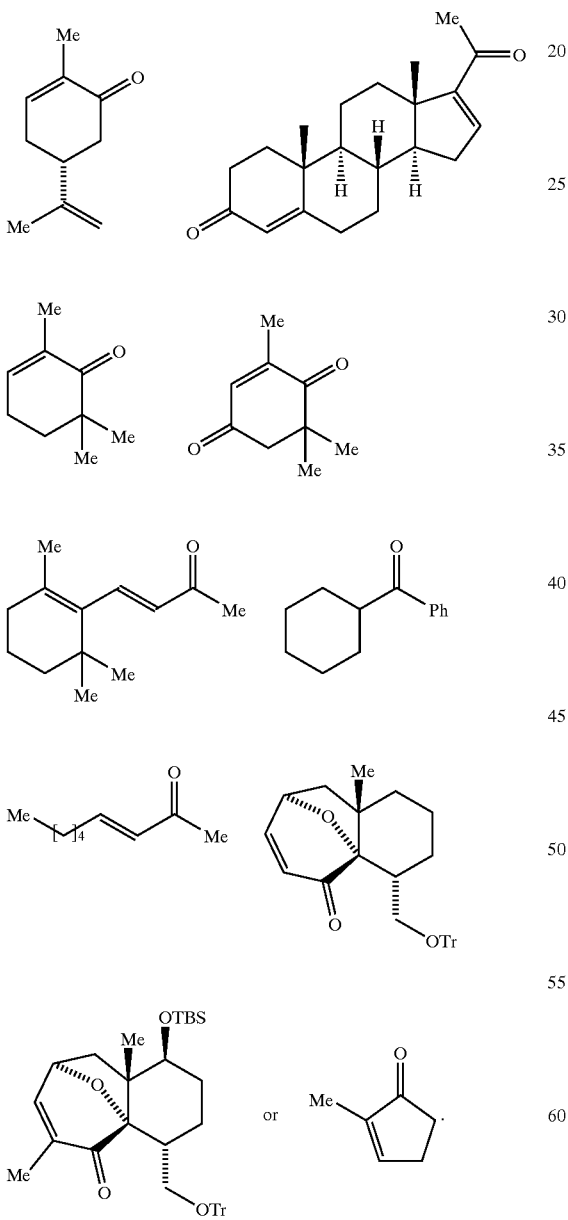

19. The method of claim 18, wherein said α,β-unsaturated ketone is 16-dehydroprogesterone.

20. A method for converting 16-dehydroprogesterone to 17 α-hydroxy progesterone comprising:
   i) obtaining said 16-dehydroprogesterone;
   ii) obtaining a catalyst of the structure:

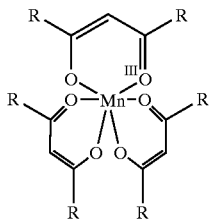

where each R is independently hydrogen, a $C_1$–$C_{20}$ linear branched or cyclic alkyl, hydroxyalkyl, glycol, polyglycol, amino, nitro, halo, cyano, aryl, heteroaryl, thio, thioalkyl, amide, ester, acyl, carboxy, —NH$_2$, —O(CH$_2$)$_n$CH$_3$ and $0 \leq n \leq 20$ or —OCH$_3$;
   iii) obtaining a reducing agent;
   iv) combining said 16-dehydroprogesterone, said catalyst and said reducing agent in the presence of dioxygen and a solvent or solvent mixture to form an α-hydroperoxyketone; and
   v) reducing said α-hydroperoxyketone to 17 α-hydroxy progesterone.

21. The method of claim 20, wherein at least one R is —H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$ or C(CH$_3$)$_3$.

22. The method of claim 20, wherein each R is the same and R is $C_1$–$C_4$ linear or branched alkyl.

23. The method of claim 20, wherein at least one R is —O(CH$_2$)$_n$CH$_3$ and $0 \leq n \leq 20$.

24. The method of claim 20, wherein at least one R is —OCH$_3$.

25. The method of claim 20, wherein at least one R is —CO(CH$_2$)$_n$CH$_3$ and $0 \leq n \leq 20$.

26. The method of claim 20, wherein R is NR'$_2$ and R' is hydrogen or $C_1$–$C_{20}$ linear, branched or cyclic alkyl.

27. The method of claim 26, wherein at least one R is —NH$_2$.

28. The method of claim 22, wherein the catalyst is tris(dipivaloylmethanato)manganese(III).

29. The method of claim 20, wherein the reducing agent is a silane.

30. The method of claim 29, wherein the reducing agent is phenyl silane.

31. The method of claim 29, wherein the reducing agent is diphenyl silane.

32. The method of claim 29, wherein the reducing agent is polymethylhydrosiloxane.

33. The method of claim 20, wherein P(OEt)$_3$ is used to reduce the α-hydroperoxy ketone.

34. The method of claim 20, wherein the solvent is isopropanol.

35. The method of claim 20, wherein the solvent is a mixture of isopropanol and 1,2-dichloroethane.

36. The method of claim 20, wherein the temperature is between 0° C. and 25° C.

37. A method for reducing β,β-disubstituted ketone or ester comprising:
   i) obtaining said β,β-disubstituted ketone or ester;
   ii) obtaining the catalyst tris(dipivaloylmethanato) manganes(III);

iii) obtaining a reducing agent;
iv) combining said ketone or ester, said catalyst and said reducing agent in the presence of dioxygen and a solvent or solvent mixture to produce a hydridic reagent capable of reducing said β,β-disubstituted ketone or ester.

38. The method of claim 37, wherein said β,β-disubstituted ketone or ester is β-ionone.

39. The method of claim 37, wherein said β,β-disubstituted ketone or ester is 16-methyl dehydroprogesterone.

40. A method for converting α,β-unsaturated esters to α-hydroxyesters comprising:
i) obtaining said α,β-unsaturated ester;
ii) obtaining a catalyst of the structure:

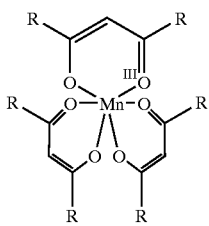

where each R is independently hydrogen, a $C_1$–$C_{20}$ linear branched or cyclic alkyl, hydroxyalkyl, glycol, polyglycol, amino, nitro, halo, cyano, aryl, heteroaryl, thio, thioalkyl, amide, ester, acyl, carboxy, —$NH_2$, —$O(CH_2)_nCH_3$ and $0 \leq n \leq 20$ or —$OCH_3$;
iii) obtaining a reducing agent;
iv) combining said ester, said catalyst and said reducing agent in the presence of dioxygen and a solvent or solvent mixture to form an α-hydroperoxyester; and
v) reducing said α-hydroperoxy ester to an α-hydroxyester.

41. The method of claim 40, wherein at least one R is —H, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$ or $C(CH_3)_3$.

42. The method of claim 40, wherein each R is the same and R is $C_1$–$C_4$ linear or branched alkyl.

43. The method of claim 40, wherein at least one R is —$O(CH_2)_nCH_3$ and $0 \leq n \leq 20$.

44. The method of claim 43, wherein at least one R is —$OCH_3$.

45. The method of claim 40, wherein at least one R is —$CO(CH_2)_nCH_3$ and $0 \leq n \leq 20$.

46. The method of claim 40, wherein R is $NR'_2$ and R' is hydrogen or $C_1$–$C_{20}$ linear, branched or cyclic alkyl.

47. The method of claim 46, wherein at least one R is —$NH_2$.

48. The method of claim 42, wherein the catalyst is tris(dipivaloylmethanato)manganese(III).

49. The method of claim 40, wherein the reducing agent is a silane.

50. The method of claim 49, wherein the reducing agent is phenyl silane.

51. The method of claim 49, wherein the reducing agent is diphenyl silane.

52. The method of claim 49, wherein the reducing agent is polymethylhydrosiloxane.

53. The method of claim 40, wherein $P(OEt)_3$ is used to reduce the α-hydroperoxy ester.

54. The method of claim 40, wherein the solvent is isopropanol.

55. The method of claim 40, wherein the solvent is a mixture of isopropanol and 1,2-dichloroethane.

56. The method of claim 40, wherein the temperature is between 0° C. and 25° C.

* * * * *

UNITED STATES PATENT AND TRADEMARK OFFICE
CERTIFICATE OF CORRECTION

PATENT NO. : 6,667,410 B2
DATED : December 23, 2003
INVENTOR(S) : Magnus et al.

It is certified that error appears in the above-identified patent and that said Letters Patent is hereby corrected as shown below:

Column 20,
Line 67, delete "manganes(III)" and insert -- manganese(III) -- therefor.

Signed and Sealed this

Sixteenth Day of March, 2004

JON W. DUDAS
*Acting Director of the United States Patent and Trademark Office*